US00PP27335P2

(12) United States Plant Patent
Berry

(10) Patent No.: US PP27,335 P2
(45) Date of Patent: Nov. 1, 2016

(54) ***LAGERSTROEMIA* PLANT NAMED 'CS2012-12'**

(50) Latin Name: ***Lagerstroemia* hybrid**
Varietal Denomination: CS2012-12

(71) Applicant: Capstone Plants Inc., Grand Saline, TX (US)

(72) Inventor: James B Berry, Mineola, TX (US)

(73) Assignee: CAPSTONE PLANTS INC., Grand Saline, TX (US)

( * ) Notice: Subject to any disclaimer, the term of this patent is extended or adjusted under 35 U.S.C. 154(b) by 0 days.

(21) Appl. No.: 14/545,923

(22) Filed: Jul. 8, 2015

(51) Int. Cl.
*A01H 5/00* (2006.01)

(52) U.S. Cl.
USPC ..... Plt./252

(58) Field of Classification Search
USPC ..... Plt./252
See application file for complete search history.

*Primary Examiner* — Annette Para
(74) *Attorney, Agent, or Firm* — Penny J. Aguirre

(57) ABSTRACT

A new cultivar of *Lagerstroemia* hybrid plant named 'CS2012-12' that is characterized by its upright, well-branched plant habit, its foliage that is a blend of bronze and green in color, its flowers that are pinkish lavender in color, its continuous flowering from mid-June to November in Texas, and its resistance to powdery mildew and leaf spot.

2 Drawing Sheets

Botanical classification: *Lagerstroemia* hybrid.
Variety denomination: 'CS2012-12'.

BACKGROUND OF THE INVENTION

The present invention relates to a new and distinct cultivar of *Lagerstroemia* of hybrid origin. The new *Lagerstroemia* will hereafter be referred to by its cultivar name, 'CS2012-12'. 'CS2012-12' is a new cultivar of crape myrtle grown for use as an ornamental landscape plant.

The new cultivar of *Lagerstroemia* is the result of a controlled breeding program conducted by the Inventor in Grande Saline, Tex. The objective of the breeding program is the develop new cultivars of crape myrtle that are disease resistant, have dark foliage, have unique flowers that bloom for an extended time, and that are well-branched with an upright plant habit.

'CS2012-12' originated as a seedling that arose from seeds pooled and sown from open pollination of numerous dark foliaged *Lagerstroemia* plants in the Inventor's breeding (all not patented) program in 2013. The parents are unknown. 'CS2012-12' was selected as a single unique plant in 2014 from amongst the resulting seedlings.

Asexual propagation of the new cultivar was first accomplished by the Inventor using stem cuttings in June of 2014 in Grand Saline, Tex. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'CS2012-12' as a unique cultivar of *Lagerstroemia*.

1. 'CS2012-12' exhibits an upright, well-branched plant habit.

2. 'CS2012-12' exhibits foliage that is bronze-green in color.
3. 'CS2012-12' exhibits flowers that are pinkish lavender in color.
4. 'CS2012-12' exhibits continuous flowering from mid-June to November in Texas.
5. 'CS2012-12' exhibits resistance to powdery mildew (*Erysiphe lagerstoemia*) and leaf spot (*Cercospora lythracearum*).

'CS2012-12' can be most closely compared to *Lagerstroemia* 'Apalachee' (not patented) and *Lagerstroemia indica* 'Potomac' (not patented). 'Apalachee' is similar to 'CS2012-12' in having flowers that are lavender in color and in having an upright habit. 'Apalachee' differs from 'CS2012-12' in having leaves that are dark green in color, in having a later starting and shorter lasting bloom period, and in being more susceptible to leaf spot. 'Potomac' is similar to 'Lavender Lace in having an upright growth habit and light grey-brown bark. 'Potomac' differs from 'CS2012-12' in having flowers that are less pink in color, in having leaves that are less bronze in color, in having a later starting and shorter lasting bloom period, and in being more susceptible to leaf spot.

BRIEF DESCRIPTION OF THE DRAWINGS

The accompanying colored photographs illustrate the overall appearance and distinct characteristics of the new *Lagerstroemia*. The photographs were taken of plants eight months in age (from a liner) as grown outdoors in three-gallon containers in Grand Saline, Tex.

The photograph in FIG. 1 provides a side view of 'CS2012-12' in bloom.

Figure 1:
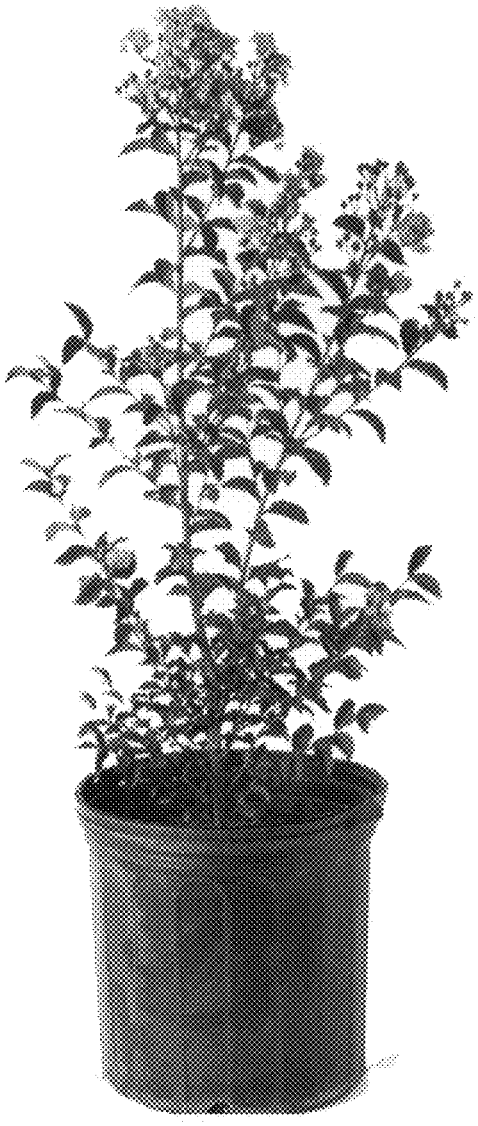
Figure 2:
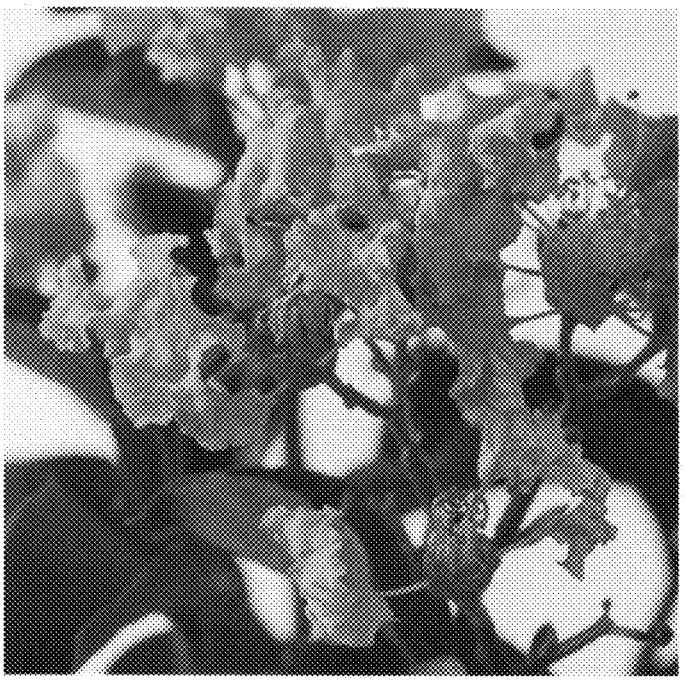

The photograph in FIG. 2 provides a close-up view of an inflorescence of 'CS2012-12'.

Figure 3:
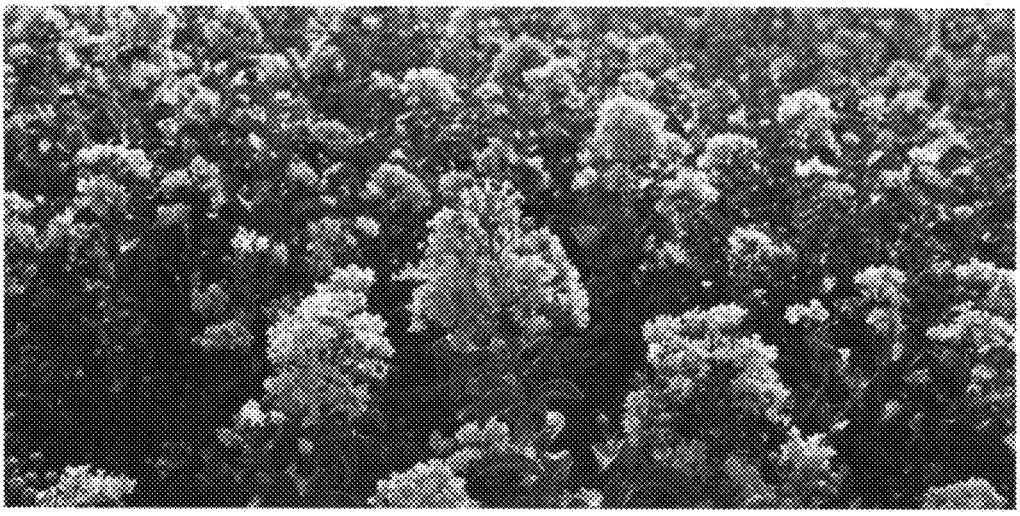

The photograph in FIG. 3 provides a view of field of blooming plants of 'CS2012-12'.

The colors in the photographs are as close as possible with the digital photography techniques available, the color values cited in the detailed botanical description accurately describe the colors of the new *Lagerstroemia*.

DETAILED BOTANICAL DESCRIPTION

The following is a detailed description of plants ten months in age (from a rooted cutting) as grown outdoors in one-gallon containers in Grand Saline, Tex. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Mid-June to November in Texas.

*Plant type.*—Perennial shrub.

*Plant habit.*—Upright, well-branched.

*Height and spread.*—An average of 50 cm in height and 23 cm in width as grown in a one-gallon container, an average of 3.7 m in height and 3 m in spread as grown in the landscape.

*Hardiness.*—At least to U.S.D.A. Zone 6.

*Diseases and pests.*—Resistance to powdery mildew (*Erysiphe lagerstoemia*) and leaf spot (*Cercospora lythracearum*) has been observed.

*Root description.*—Fibrous and fine.

*Root development.*—An average of 2 weeks for root initiation and about 5 weeks to produce a young rooted plant.

*Propagation.*—Stem cuttings.

*Growth rate.*—Vigorous.

Stem description:

*Shape.*—Quadrangulate with slight wings.

*Stem color.*—187B.

*Stem size.*—Main lateral branches; an average of 48 cm in length and 3 mm in diameter, secondary branches; average of 10 cm in length and 2 mm in width.

*Stem surface.*—Slightly pubescent.

*Stem strength.*—Strong.

*Branching.*—An average of 4 lateral branches with 2 to 3 secondary branches.

*Internode size.*—An average of 2.2 cm.

*Stem fragrance.*—Fragrance typical for *Lagerstroemia* detected when touched (musty).

Foliage description:

*Leaf shape.*—Elliptic.

*Leaf division.*—Single.

*Leaf base.*—Cuneate.

*Leaf apex.*—Acute to slightly acuminate.

*Leaf venation.*—Pinnate, color mid rib; upper surface 183B and lower surface 179C, other veins primarily match leaf coloration.

*Leaf margins.*—Entire, slightly undulate.

*Leaf arrangement.*—Opposite to nearly opposite.

*Leaf attachment.*—Petiolate.

*Leaf surface.*—Both surfaces moderately covered with glands, minute in size, and colored the same as the leaf surface.

*Leaf size.*—An average of 4.6 cm in length and 2 cm in width.

*Leaf quantity.*—An average of 22 (11 pairs) per branch 33 cm in length.

*Leaf color.*—Young and mature leaves upper surface; a blend of 147A and 187A, young mature leaves lower surface; 144B, mature growth upper surface; a blend of 137A and 187B.

*Leaf fragrance.*—Fragrance typical for *Lagerstroemia* detected when touched.

*Petioles.*—An average of 1 mm in length and width and 187B in color, surface texture glabrous.

Flower description:

*Inflorescence type.*—Two to three flowers at upper nodes with terminal corymb.

*Lastingness of inflorescence.*—About one week.

*Inflorescence size.*—An average of 9 cm in height and 6 cm in width including flowers at nodes.

*Inflorescence number.*—An average of 1 per lateral stem, with occasional lower branch with 2-flowers.

*Flower number.*—An average of 18 flowers per inflorescence.

*Flower fragrance.*—Mild sweet scent.

*Flower buds.*—Flattened globular in shape, an average of 8 mm in diameter and 7 mm in depth, surface; satiny, color; 174C with margins on immature sepals 174A.

*Flower aspect.*—Upright to outward.

*Flower type.*—Rotate.

*Flower size.*—An average of 4 cm in diameter and 1.5 cm in depth.

*Petals.*—An average of 6, ovate in shape, strongly undulate crenate margins, stalked base (attached between sepals), rounded apex, both surfaces glabrous and dull, an average of 1.7 cm in length and 1.2 cm in width (stalk portion is about 4 mm in length and <1 mm in width), color when opening and when fully open upper and lower surface; a blend of 70A and 70B with stalk 64A, petal color does not fade.

*Calyx.*—Campanulate in shape, an average of 7 mm in length and 1.1 cm in diameter.

*Sepals.*—An average of 6, fused at base with tips spreading outward, elliptic in shape, entire margins, acuminate-acute apex to tips, both surfaces smooth and dull, an average of 7 mm in length and 3 mm in width (free apex portion is 3 mm in length and width), color; upper and lower surface when opening and when fully open is 161A and suffused with 174A.

*Peduncles.*—Strong, an average of 1.3 cm in length and 1.5 mm in width, 174A in color, surface is slightly glossy, terminal peduncles held at an average angle of 0° to the lateral branch, secondary peduncles and those at lower nodes are held at an average angle of 45° to the lateral branch.

*Pedicels.*—Strong, an average of 9 mm in length and 1 mm in width, 161A and suffused with 174A, held at an average angle of 45° to peduncle.

Reproductive organs:

*Stamens.*—Average of 22, anther; an average of 1.5 mm in length, dorsifixed, oblong in shape, 147A in color, filament; an average of 7 mm in length and 157C in color, pollen is abundant in quantity and 15A in color.

*Pistils.*—An average of 1, an average of 1.6 cm in length, style; an average of 1.5 cm in length and 179A in color, stigma is club-shaped, 1 mm in length and 147A in color, ovary is globose in shape, 2 mm in diameter and 160B in color.

*Seed and fruit.*—None observed to date.

It is claimed:

1. A new and distinct cultivar of *Lagerstroemia* plant named 'CS2012-12' as herein illustrated and described.

* * * * *